US010983065B2

(12) United States Patent
Burg et al.

(10) Patent No.: US 10,983,065 B2
(45) Date of Patent: Apr. 20, 2021

(54) METHOD, APPARATUS AND SYSTEM FOR DETECTING AND DETERMINING COMPROMISED REAGENT PADS BY QUANTIFYING COLOR CHANGES INDUCED BY EXPOSURE TO A HOSTILE ENVIRONMENT

(71) Applicant: HEALTHY.IO LTD., Tel Aviv-Jaffa (IL)

(72) Inventors: Bernard Burg, Menlo Park, CA (US); Martin Zizi, Enines (BE); Walter De Brouwer, Los Altos, CA (US); Jaime Tenedorio, Portola Valley, CA (US); Babak Aghazadeh, Fremont, CA (US); Jie Cui, Sunnyvale, CA (US); Sheena Menezes, Los Gatos, CA (US)

(73) Assignee: HEALTHY.IO LTD., Tel Aviv-Jaffa (IL)

( * ) Notice: Subject to any disclaimer, the term of this patent is extended or adjusted under 35 U.S.C. 154(b) by 0 days.

(21) Appl. No.: 16/246,406

(22) Filed: Jan. 11, 2019

(65) Prior Publication Data

US 2020/0225166 A1 Jul. 16, 2020

Related U.S. Application Data

(63) Continuation of application No. 15/289,961, filed on Oct. 10, 2016, now abandoned, which is a
(Continued)

(51) Int. Cl.
*G01N 21/78* (2006.01)
*G01N 21/79* (2006.01)
(Continued)

(52) U.S. Cl.
CPC ......... *G01N 21/8483* (2013.01); *G01N 21/78* (2013.01); *G01N 21/79* (2013.01);
(Continued)

(58) Field of Classification Search
CPC ........ G01N 21/77; G01N 21/78; G01N 21/79; G01N 21/80; G01N 21/81; G01N 21/8483;
(Continued)

(56) References Cited

U.S. PATENT DOCUMENTS 4,541,987 A * 9/1985 Guadagno ............ G01N 33/725
422/401
4,904,605 A * 2/1990 O'Brien ................ G01N 33/18
356/421
(Continued)

FOREIGN PATENT DOCUMENTS

DE 102010011838 A1 9/2011
KR 1020100008840 A 1/2010
(Continued)

*Primary Examiner* — Maureen Wallenhorst
(74) *Attorney, Agent, or Firm* — Finnegan, Henderson, Farabow, Garrett & Dunner, LLP

(57) ABSTRACT

A reagent test paddle includes a contamination detection medium, a reference color bar, at least one chemical test medium, and a unique identifier. The contamination detection medium includes a reagent that changes color in the presence or when exposed to a hostile or inhospitable environment. Each chemical test medium includes a regent that is responsive to a respective analyte in a biological sample. The reference color bar includes reference color samples of different colors. The unique identifier, like a serial number, identifies the particular paddle and its chemical test medium so it can be uniquely and anonymously associated with a user. A method includes capturing and interpreting digital images of a biologically unexposed and subsequently exposed reagent test paddle at various delay
(Continued)

times within an automatically calibrated environment; locating the paddle in a plurality of digital images, extracting the reference color bar and locating the contamination detection medium and chemical test medium in each digital image. Color changes of the chemical test medium and contamination medium are detected at various delay times after sample exposure. To determine validity of test results, the method further compares the detected colors of the contamination detection medium with predetermined colors expected for no contamination and contamination.

10 Claims, 10 Drawing Sheets

Related U.S. Application Data continuation-in-part of application No. 14/639,509, filed on Mar. 5, 2015, now Pat. No. 9,528,941, and a continuation-in-part of application No. 14/419,939, filed as application No. PCT/US2013/035397 on Apr. 5, 2013, now Pat. No. 9,311,520.

(60) Provisional application No. 61/948,536, filed on Mar. 5, 2014, provisional application No. 61/680,842, filed on Aug. 8, 2012.

(51) Int. Cl.
*G01N 21/80* (2006.01)
*G01N 21/81* (2006.01)
*G01N 21/84* (2006.01)
*G01N 33/52* (2006.01)
*G06T 7/90* (2017.01)

(52) U.S. Cl.
CPC .............. *G01N 21/80* (2013.01); *G01N 21/81* (2013.01); *G01N 33/52* (2013.01); *G06T 7/90* (2017.01); *G01N 2021/8488* (2013.01); *G01N 2021/8494* (2013.01)

(58) Field of Classification Search
CPC ........... G01N 33/52; G01N 2021/8488; G01N 2021/8494; G06T 7/90
USPC ......... 436/164, 165, 169; 422/400, 420, 430
See application file for complete search history.

(56) References Cited

U.S. PATENT DOCUMENTS

| | | | | |
|---|---|---|---|---|
| 4,911,344 | A * | 3/1990 | Kahler | B01L 99/00 221/135 |
| 5,408,535 | A | 4/1995 | Howard, III et al. | |
| 6,285,454 | B1 | 9/2001 | Douglas et al. | |
| 9,958,361 | B2 * | 5/2018 | Cotton | G01N 33/521 |
| 2002/0086435 | A1 * | 7/2002 | Fernandez Decastro | G01N 33/526 436/164 |
| 2003/0133847 | A1 * | 7/2003 | Hagen | G01N 33/48757 422/430 |
| 2005/0157304 | A1 | 7/2005 | Xiao et al. | |
| 2006/0292040 | A1 | 12/2006 | Wickstead et al. | |
| 2008/0227216 | A1 * | 9/2008 | Albeck | G01N 31/22 436/165 |
| 2011/0275104 | A1 * | 11/2011 | Zimmerle | G01N 33/523 435/23 |
| 2012/0063652 | A1 * | 3/2012 | Chen | G01N 21/274 382/128 |
| 2012/0106811 | A1 | 5/2012 | Chen et al. | |
| 2012/0178101 | A1 | 7/2012 | Bae et al. | |
| 2012/0251409 | A1 * | 10/2012 | Hrboticka | G01N 31/22 422/401 |
| 2012/0282154 | A1 | 11/2012 | Slowly et al. | |
| 2014/0242612 | A1 | 8/2014 | Wang et al. | |
| 2018/0024073 | A1 * | 1/2018 | Schornstein | B01L 3/502 436/169 |

FOREIGN PATENT DOCUMENTS

| | | |
|---|---|---|
| KR | 1020110024747 A | 3/2011 |
| WO | WO 2007/079843 A2 | 7/2007 |

\* cited by examiner

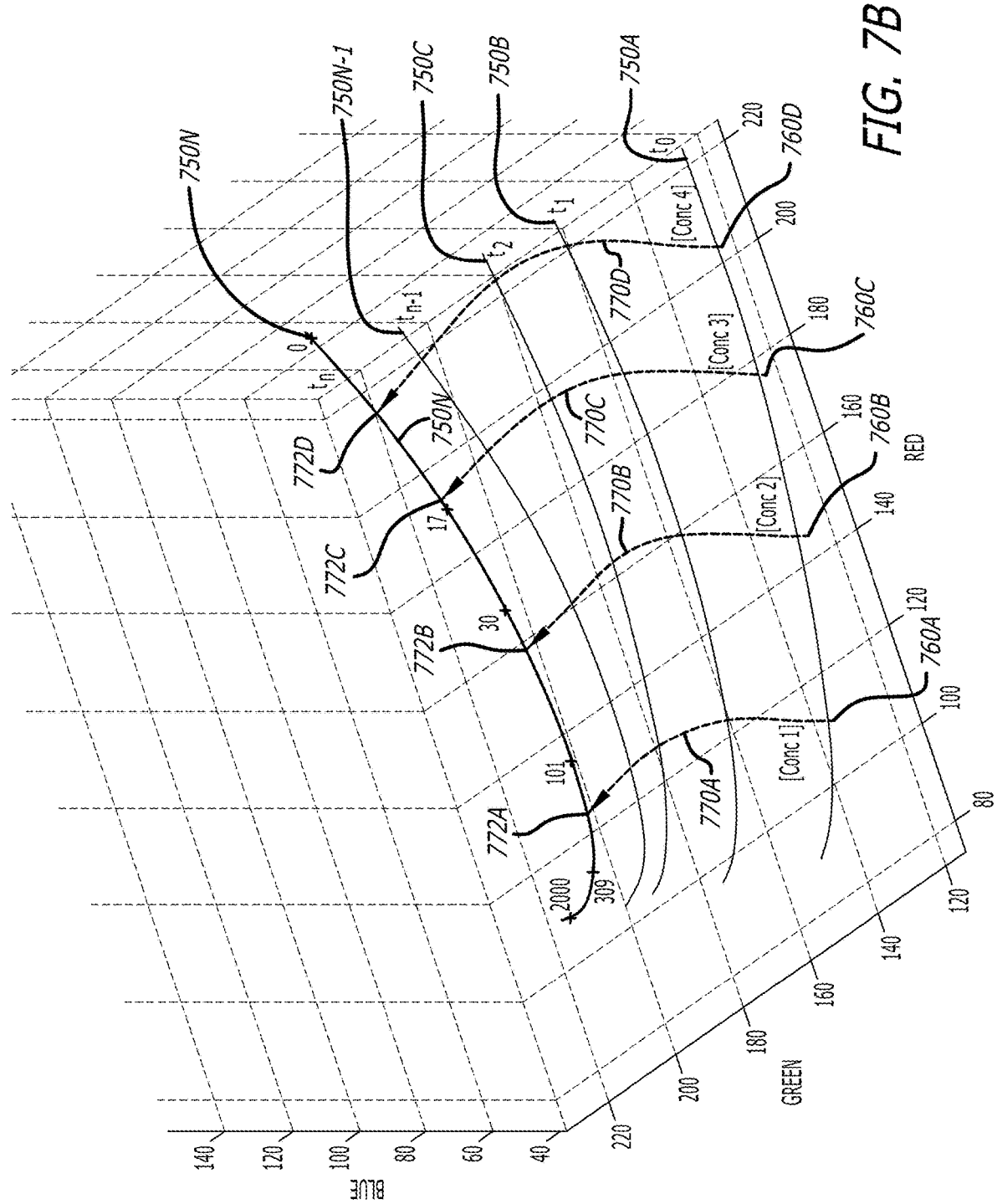

METHOD, APPARATUS AND SYSTEM FOR DETECTING AND DETERMINING COMPROMISED REAGENT PADS BY QUANTIFYING COLOR CHANGES INDUCED BY EXPOSURE TO A HOSTILE ENVIRONMENT

CROSS REFERENCE TO RELATED APPLICATIONS

This application is a divisional application that claims the benefit of United States (US) Non-Provisional Patent application Ser. No. 15/289,961 (now abandoned) entitled METHOD AND APPARATUS FOR DETERMINING ANALYTE CONCENTRATION BY QUANTIFYING AND INTERPRETING COLOR INFORMATION CAPTURED IN A CONTINUOUS OR PERIODIC MANNER filed Oct. 10, 2016 by inventors Bernard Berg et al. U.S. patent application Ser. No. 15/289,961 is a continuation in part (CIP) and claims the benefit of United States (US) Non-Provisional Patent application Ser. No. 14/639,509 (now U.S. Pat. No. 9,528,941) entitled METHOD AND APPARATUS FOR DETERMINING ANALYTE CONCENTRATION BY QUANTIFYING AND INTERPRETING COLOR INFORMATION CAPTURED IN A CONTINUOUS OR PERIODIC MANNER filed Mar. 5, 2015. U.S. patent application Ser. No. 14/639,509 claims the benefit of U.S. Provisional Patent Application No. 61/948,536 entitled APPARATUS FOR DETERMINING ANALYTE CONCENTRATION BY QUANTIFYING AND INTERPRETING COLOR INFORMATION CAPTURED IN A CONTINUOUS OR PERIODIC MANNER filed Mar. 5, 2014, which is hereby incorporated by reference in its entirety for all intents and purposes.

Furthermore, U.S. patent application Ser. No. 14/639,509 (now U.S. Pat. No. 9,528,941) is a CIP claiming the benefit of U.S. patent application Ser. No. 14/419,939 (now U.S. Pat. No. 9,311,520) entitled METHOD AND APPARATUS FOR PERFORMING AND QUANTIFYING COLOR CHANGES INDUCED BY SPECIFIC CONCENTRATIONS OF BIOLOGICAL ANALYTES IN AN AUTOMATICALLY CALIBRATED ENVIRONMENT filed Feb. 6, 2015. U.S. patent application Ser. No. 14/419,939 is a national phase application claiming priority to Patent Cooperation Treaty (PCT) Application No. PCT/US2013/035397 entitled METHOD AND APPARATUS FOR PERFORMING AND QUANTIFYING COLOR CHANGES INDUCED BY SPECIFIC CONCENTRATIONS OF BIOLOGICAL ANALYTES IN AN AUTOMATICALLY CALIBRATED ENVIRONMENT filed Apr. 5, 2013. PCT Application No. PCT/US2013/035397 claims the benefit of U.S. Provisional Patent Application No. 61/680,842 entitled MULTI-ANALYTE RAPID DIAGNOSTIC TEST AND METHOD OF USE filed Aug. 8, 2012.

FIELD

The embodiments relate generally to systems, methods, and apparatus for detecting the presence or absence of exposure of a reagent pad to a hostile environment compromising the reliability of determining the presence or absence and concentration of a variety of analytes in a fluid sample.

BACKGROUND

Reagent dipsticks and immunoassays have been used in medical clinics for decades in connection with methods for rapidly diagnosing health conditions at the point of care. In a clinical environment, dipsticks have been used for the diagnosis of urinary tract infections, preeclampsia, proteinuria, dehydration, diabetes, internal bleeding and liver problems. As is known, dipsticks are laminated sheets of paper containing reagents that change color when exposed to an analyte solution. Each reagent pad on the dipstick is chemically treated with a compound that is known to change color in the presence of particular reactants. For example, in the context of urinalysis, the dipstick will typically include reagent pads for detecting or measuring analytes present in a biological sample such as urine, including glucose, bilirubin, ketones, specific gravity, blood, pH, protein, urobilirubin, nitrite, leukocytes, microalbumin and creatinin.

In a clinical environment, after exposing dipsticks to a test sample solution, automatic methods and apparatus for interpreting test results of dipsticks with immunoassays are often utilized. The apparatus for interpreting test results are generally referred to as a laboratory diagnostic instrument. Before a dipstick is exposed to the test sample solution, it may be exposed to a hostile environmental condition, such as humidity by improper handling from failing to recap or completing tighten the strip bottle. Exposure to hostile environmental conditions can compromise the integrity of a dipstick, leading to false results and possibly an incorrect diagnosis.

The problem with integrity is even greater with in home or at home health diagnostic kits. Recently, at home health diagnostic kits have been introduced to help determine or diagnose health conditions of a user by performing at home testing. At home health diagnostics can help diagnose certain health problems quickly, substantially reduce costs, save travel time, and avoid the inconvenience of testing subjects in a clinical environment. However, at home health diagnostics can possibly lead to an incorrect diagnosis when exposed to hostile environmental conditions such as by improper handling by the user or damage during transportation, for example.

It is desirable to improve home health diagnostic kits to lower the probability of making an incorrect diagnosis.

BRIEF SUMMARY

Generally disclosed are a method, apparatus, and system for performing automatic detection of compromised reagent pads exposed to a hostile environment. The method, apparatus, and system permit the automatic capture of a digital image of a diagnostic instrument with a contamination detection medium containing a reagent. The contamination detection medium may have been exposed to a hostile environment before being exposed to the biological sample. The method, apparatus, and system determine whether the diagnostic instrument has been exposed to a hostile environment that makes the undergoing test result unreliable and invalid. The method, apparatus, and system detect the contamination by quantifying color changes induced by the exposure of the detection medium reagent pads to a hostile environment. The quantification of color change is based on an automatic calibrating protocol, independent of lighting variations in the external environment. Accurate, precise, and cost effective measurements are provided while minimizing user interaction with biological samples. The method aims to minimize errors to support medical scientific instruments.

Therefore, according to one embodiment, a computer-implemented method for determining exposure of a diagnostic instrument to a hostile environment is disclosed. The method includes capturing a digital image of at least a portion of the diagnostic instrument at one or more unique time points before and or after being exposed to a biological sample undergoing tests. The diagnostic instrument includes at least one reference color bar including a plurality of reference color samples, at least one test medium having a reagent that changes color in the presence of particular analytes in a biological sample, and at least one contamination detection medium having a reagent. The reagent may change color when being exposed to a hostile environment. Alternatively, the reagent may show a different color when being exposed to particular analytes in a biological sample after exposure to the hostile environment. The hostile environment is usually brought about by accident and not intentionally. The hostile environment can be humidity or moisture. Another source of hostile environment may be a biological hazard (biohazard) contamination of the test paddle reagents resulting from contact with a human body, other than the biological sample being tested, such as a finger with a contaminant, such as oil secretion. Another source of a hostile environment may be a chemical hazard contamination of the test paddles reagents such as by dust, dirt, or grime in the air or a surface (turned upside down onto the surface) to which the reagents of the test paddle are exposed. Any other possible exposure to chemical or biological hazards in the process of manufacturing, packaging, shipping, and handling of test instruments which change the chemical nature of the reagents may be considered a hostile environment if it makes the test result unreliable and invalid. The method further includes identifying at least one reference sample of the plurality of reference samples in the diagnostic instrument; determining a dominant camera-captured color of a reference sample and a dominant camera-captured color of at least one contamination detection medium; color correcting the dominant camera-captured color of at least one contamination detection medium to determine a first corrected contamination detection medium color in response to a correction factor derived at least in part from the dominant camera-captured color of the reference sample; and comparing the corrected contamination detection medium color to a pair of predetermined possible contamination detection medium colors to determine an exposure detection result.

In accordance with another embodiment, a digital image of at least a portion of the diagnostic instrument is captured before the instrument is exposed to a biological sample material or biological sample fluid that is desirable to test. A dominant camera-captured color of at least one contamination detection medium is corrected in response to the color reference sample associated with at least one dominant camera-captured color of the color reference. The color reference includes a plurality of reference samples of different colors. The corrected contamination detection medium color is compared to a predetermined exposure detection color range stored in the diagnostic system. The predetermined exposure detection color range is for a time point and color point prior to the test instrument being exposed to the biological sample. If there is a substantial deviation in the corrected contamination detection medium color from the predetermined exposure detection color range, the system and method determines there is contamination, alerts the user to such exposure, and terminates any undergoing test. The system and method can further send out a message as a reminder to the user to change out the contaminated diagnostic instrument.

In accordance with another embodiment, a digital image of at least a portion of the diagnostic instrument is captured immediately after the test instrument has been exposed to a biological sample that is being tested. A dominant camera-captured color of at least one contamination detection medium is corrected in response to the color reference associated with at least one dominant camera-captured color of the color reference. The color reference comprises a plurality of reference samples of different colors. The corrected contamination detection medium color is compared to a predetermined exposure detecting color range stored in the diagnostic system. The predetermined exposure detection color range is for a time point and color point at a beginning stage of the test instrument being exposed to a biological sample that is being tested. If there is a substantial deviation in the corrected contamination detection medium color from the predetermined exposure detection color range, the system and method determines there is contamination, alerts the user to such exposure, and terminates any undergoing test. The system and method can further send out a message as a reminder to the user to change out the contaminated diagnostic instrument.

In accordance with a further embodiment, a first digital image of at least a portion of the diagnostic instrument is captured before the test instrument has been exposed to a biological sample that is to be tested. A second digital image of at least a portion of the diagnostic instrument is captured after the test instrument has been exposed to a biological sample under test. A contamination detection medium and test reagent media of the test instrument undergo chemical reactions with the biological material/fluid being tested. The method further includes determining a corrected dominant camera-captured color of at least one contamination detection medium for each of the first and second captured digital images; calculating a mathematical difference between the two corrected dominant camera-captured colors of the contamination detection medium in the two captured digital images; and comparing the calculated difference between the two corrected dominant camera-captured colors of the contamination detection medium to a predetermined possible exposure detection value range to determine an exposure detecting result.

In accordance with a further embodiment, a first digital image of at least a portion of the diagnostic instrument is captured after the test instrument has been exposed to a biological sample being tested for a short period of time, and a second digital image of at least a portion of the diagnostic instrument is captured after the test instrument has been exposed to the biological sample being tested for an additional period of time. The contamination detection medium and test reagent media undergo chemical reactions with the biological sample being tested that are completed after the additional period of time. The method further includes determining a corrected dominant camera-captured color of at least one contamination detection medium for each of the first and second digital images respectively; calculating a difference between the two corrected dominant camera-captured colors of the contamination detection medium in the two captured digital images; and comparing the calculated difference between the two corrected dominant camera-captured colors of the contamination detection medium to a predetermined possible exposure detection value range to determine an exposure detection result.

These and other features and characteristics of the embodiments, as well as the methods of operation and functions of the related elements of structures and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and the claims, the singular form of "a", "an", and "the" include plural referents unless the context clearly dictates otherwise.

BRIEF DESCRIPTION OF THE DRAWINGS

For the purpose of facilitating understanding of the embodiments, the accompanying drawings and description illustrate the various structures, construction and methods of operation, and many advantages that may be understood and appreciated.

FIG. 7B is a three dimensional red, green, blue (RGB) color space graph showing a color trajectory of a chemical reaction between contamination detection reagent and an analyte at multiple concentrations.

DETAILED DESCRIPTION

Figure 1:
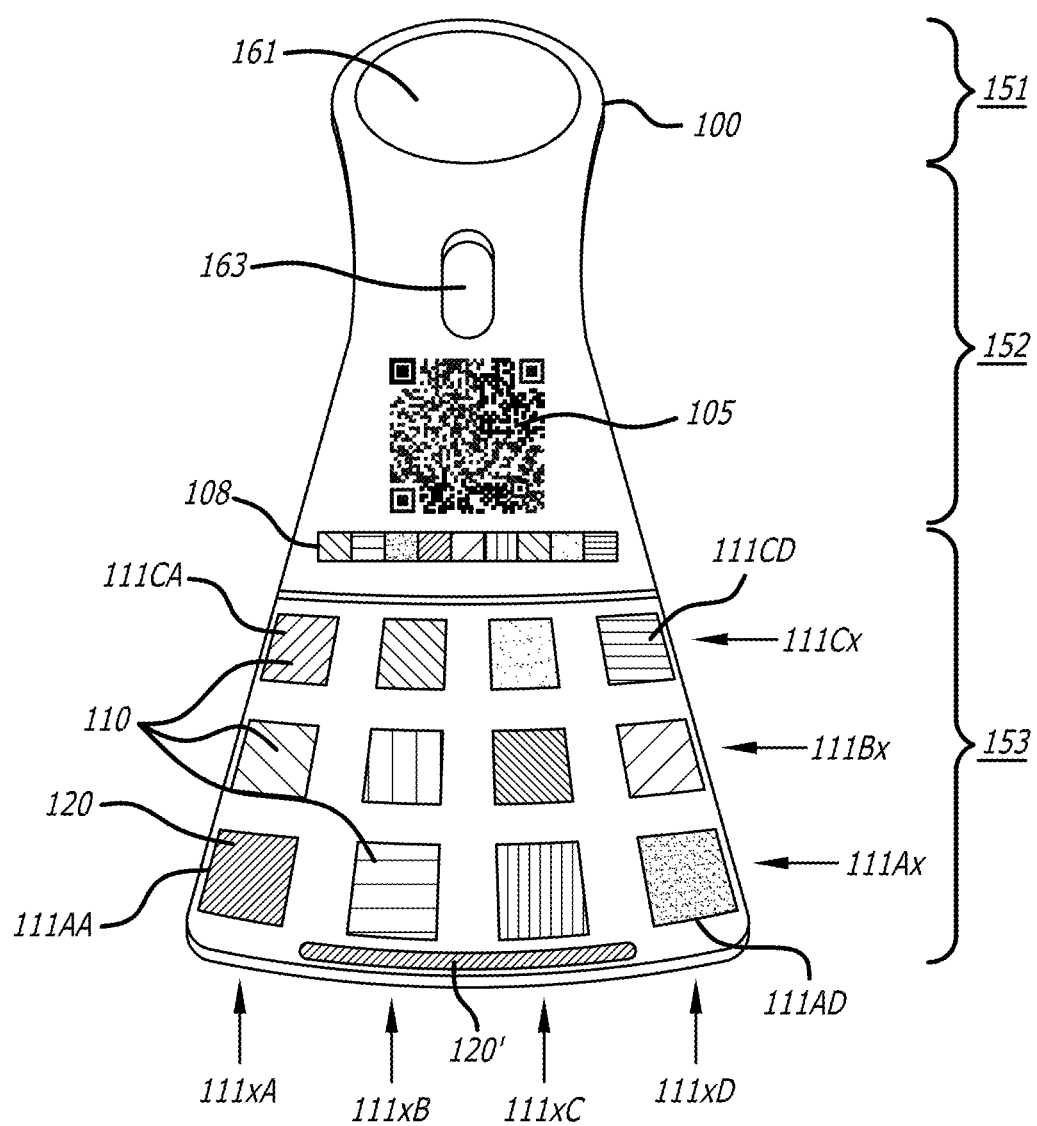
FIG. 1 is a top view of a diagnostic instrument (reagent paddle) with a plurality of reagent test pads, a plurality of reference samples of different colors, and an exposure detecting pad to provide a system for analyzing a biological sample over time with automated detection of exposure to hostile environments.

In the following detailed description of the embodiments, numerous specific details are set forth in order to provide a thorough understanding. However, it will be obvious to one skilled in the art that the embodiments may be practiced without these specific details. In other instances, well known methods, procedures, components, and circuits have not been described in detail so as not to unnecessarily obscure aspects of the embodiments of the invention. Furthermore, points and curves disclosed by the figure and described herein are examples for explanatory purposes. Actual points and curves of measured colors will vary.

The embodiments of the invention include a method, apparatus and system to detect and determine exposure of a sensitive diagnostic instrument to hostile environmental conditions. The sensitive diagnostic instrument is used to quantify photometric reactions to biological samples over a period of time.

Reagent dipsticks and immunoassays have been used in medical clinics for decades in connection with methods for rapidly diagnosing or monitoring health conditions at the point of care or at the doctor's office.

In a clinical environment, dipsticks have been used for the diagnosis of urinary tract infections, preeclampsia, proteinuria, dehydration, diabetes, internal bleeding and liver problems. As is known, dipsticks are laminated sheets of paper containing reagents that change color when exposed to an analyte-containing solution. Each reagent pad on the dipstick is chemically treated with a compound that is known to change color in the presence of particular reactants. For example, in the context of a urinalysis, the dipstick will include reagent pads for detecting or measuring analytes present in a biological sample, in this case urine, including glucose, bilirubin, ketones, specific gravity, blood, pH, protein, urobilinogen, nitrite, leukocytes, microalbumin and creatinin. Other types of dry solid chemical test pads may be formed, such as chemical test pads with biomarkers for drug use monitoring, and chemical test pads with Prostate Specific Antigen (PSA) for prostate cancer.

In Patent Cooperation Treaty (PCT) Application No. PCT/US2013/035397 (nation phase—U.S. patent application Ser. No. 14/419,939) to which priority is claimed (hereinafter "the Burg 397"), an automated method is disclosed to interpret color change of an exposed dipstick and immunoassay in a continuous or periodic manner. The method reports on multiple possible reactions and/or intermediate reaction rates. Digital image analyzing methods have a need to automatically check whether the diagnostic instrument has been exposed to a hostile environment and whether its reagent pads have been contaminated. Contaminated pads can cause a false change of colors in the pad reagents leading to false results and false diagnosis.

The embodiments of the invention include a method and apparatus that periodically monitors the color changes of at least one contamination detection reagent pad and reagent test pads over time of the chemical reactions. The contamination detection reagent pad is monitored to provide an optimal color interpretation at several points of time of the chemical reaction, e.g. before the chemical reaction, at the beginning stage of the chemical reaction, in the middle of the chemical reaction, and towards the end of the chemical reaction. Color interpretation is augmented by taking a color time-gradient into account. A chemical reaction rate model is approximated to yield a higher interpretation precision of color interpretation. At any points of time of the color interpretation procedure, once the contamination detection reagent pad is detected and determined to be exposed to a hostile environment, the system ceases the diagnostic procedure and alerts users on invalid results.

Embodiments of the invention also provide improved accuracy of the detection through better color correction, and error reduction using statistical methods to cross reference common factors such as time, temperature, and acidity (pH) of chemical reactions on chemical test pads on a paddle. Precision/accuracy is improved by modeling the chemical reaction rate of the contamination detection reagent pad, and providing better color correction and superior reaction calibrations.

Some embodiments of the invention also provide a user friendly interactive user interface. A user interface is provided to hold user attention with real-time interpretations. Based on the results of the detection, the user interface either shows messages regarding invalid results with a reminder to change the test paddle, or allows users to observe the reagents reactions, helping them to continue focusing their attention on the process.

A platform of generic open photometry tools is disclosed herein. As defined herein, open photometry is a photometer that does not require shielding from interfering photonic pollution, hence open photometers do not require an enclosure with a fixed light path. Problems such as ambient light levels, fluid sample handling, and color correction have been described in Burg '397, as applied to the particular application for performing and quantifying color changes induced by specific concentrations of biological analytes in an automatically calibrated environment. In particular, the methods described in Burg '397 for working in uncontrolled lighting conditions include capturing color images by making geometric corrections, performing color corrections, establishing color calibration trajectories, and comparing colors taken in uncontrolled lighting conditions to the established color trajectories.

One aspect of embodiments of the invention augments the existing capabilities of the method and device described in Burg '397 by extending the apparatus towards a portable electronic device capable of capturing sequences of images and displaying the progress of the reactions and results therefrom in near-real time. When using a portable electronic device to capture digital images of the paddle, the digital images are captured without controlled lighting conditions or closed system lighting environments. Color matching and color corrections are significantly more complex when trying to capture images in uncontrolled lighting environments. Thus, sequences of images of the changing color of test pads are captured at a plurality of time points and analyzed to improve diagnostic results of measured concentrations of various analytes in a biological sample and improve the detection of contamination and invalid results.

Another aspect of some embodiments of the invention is to augment the reality perceived by a user by processing the perceived sequence of images and displaying the progress of the reactions in near-real time on the image capturing device.

Referring now to FIG. 1, a reagent paddle 100 with reagents pads arranged in three rows (111Ax-111Cx) and four columns (111xA-111XD) is shown. The reagent paddle 100 includes at least one contamination detection reagent pad 120. At least one contamination detection reagent pad 120 may be positioned near the bottom corner of the reagent paddle 100 in position 111AA for example. The reagent paddle 100 further includes a plurality of reagent pads 110 in other positions on the array of pads near the bottom of the paddle 100, such as those in rows (111Bx-111Cx) and columns (111xB-111xD). The reagent pads 110 may also referred to as chemical test pads (CTP) or simply test pads herein. A contamination detection reagent bar 120' may be alternatively and/or additionally positioned outside the array of pads arranged in three rows (111Ax-111Cx) and four columns (111xA-111XD). At least one contamination detection reagent pad 120 and the contamination detection reagent bar 120' are simply referred together hereafter as a contamination detection reagent pad 120.

The paddle 100 may further include an identifier 105, such as a quick response (QR) code 105 to automatically identify the paddle 100. The QR code 105 may be configured to contain certain identification information about the paddle 100, such as a list of the analytes that are being tested, expiration date of the paddle 100, the conditions that are being tested, and other identifying information. The identification information may also be printed directly on the identifier or encrypted within the QR code 105. The identifier 105 may also be used to associate the paddle and test results to a user.

Alternatively, the QR code 105 may be associated with information stored elsewhere, such as is the case with bar codes or other short distance data exchange devices and methods. The identification information may be used in validation processes to ensure the diagnostic paddle 100 is suitable for the tests being performed and to ensure that it is safe to use, in good working condition, or to resolve other issues which may impact quality and reliability of the test results.

The paddle 100 may also include a reference color bar (RCB) 108. The RCB 108 includes a plurality of color samples of different colors in a side-by-side linear arrangement. For example, the RCB 108 may include color samples for one or more of the following colors: Cyan, Magenta, Yellow, Key (black), Gray, White, Red, Green, and Blue. The color sample colors of the RCB 108 correspond with common color spaces, such as Red-Green-Blue, Cyan-Magenta-Yellow-Key (CMYK), pantone, Munsell, International Commission on Illumination (CIE) XYZ, or the International Color Consortium (ICC) device independent color space (L*a*b color space). The RCB 108 is used for image processing, specifically to calibrate a digital image to improve the quality and accuracy of color analysis.

The paddle 100 is generally formed of a substrate including a handle 151 and a test portion 153 coupled together by a neck 152. The handle 151 near a proximal end includes a finger opening 161 into which fingers can be inserted to hold on to the paddle 100. The test portion 153 located near a distal end of the paddle 100 is dipped into a biological sample. The neck 152 distances the handle 151 of the paddle from the test portion 153 so that the handle is not exposed to the biological sample.

The neck 152 of the paddle 100 may optionally include a slot 163 to show lateral flow test results. The identifier 105 and reference color bar 108 may also be coupled to the neck 152 of the paddle 100. The reference color bar (RCB) 108 may be located adjacent the identifier 105 in the neck of the paddle as shown or wrapped around and surrounding the RCB 108.

The reagent paddle 100 is typically sealed in a bag prior to shipment to an in-home or at-home user. Prior to use, the bag is unsealed and the reagent paddle 100 is removed from the bag. Before exposure to a biological sample, such as during assembly, packaging, or shipping, the contamination detection reagent pad 120,120' changes color if the reagent paddle 100 has been accidentally exposed to a hostile environment, such as humidity, chemicals, etc. Accordingly, a single digital image (digital photo) or a plurality of digital images (digital video) of the paddle 100 can be captured by an electronic device, prior to the paddle 100 being exposed to the biological sample.

If the reagent paddle 100 has not been exposed to the expected hostile environments, the contamination detection reagent pad 120 is not expected to change color before use. Analysis of the single digital image (digital photo) or the plurality of digital images (digital video) of the paddle 100 can readily detect a color in the contamination detection reagent pad 120 before use. For example in FIG. 8, the contamination detection reagent pad 120 may be shipped from the factory with a color at an uncontaminated color point 800 (e.g., white) indicating that no hostile environment has been indicated. After exposure to a hostile environment and before exposure to a biological sample, the color of the contamination detection reagent pad 120 may have changed to a contaminated color point 805A for example. The difference between color values of color point 800 and color point 805A can readily indicate that the contamination detection reagent pad 120 has been exposed to a hostile environment before exposure to a biological sample.

In some cases, the hostile environment may be so subtle that it does not initially cause a color change in the contamination detection reagent pad 120 before being exposed to the biological sample. In some cases, a user may forget to capture a digital image prior to exposure to the biological sample. In some cases, contamination from a hostile environment may happen after the first digital image (digital photo) of the paddle is captured but prior to the reagent paddle 100 exposure to the biological sample. Mishandling can happen after taking a first digital image (digital photo) and collecting the biological sample. A user may perform a hand washing procedure required by the at-home diagnostics that poses a high risk of exposing the reagent paddle 100 to humidity. In other cases, the contamination from the hostile environment may happen after the contamination detection reagent pad 120 has been intentionally exposed to the biological sample.

After an initial contamination detection process or not, a user can expose the contamination detection reagent pad 120,120' and the plurality of reagent pads 110 of the reagent paddle 100 to a biological sample. If the CTPs 110 undergo chemical reactions with the applied biological sample, they change color over a brief period of time in response to concentrations of various analytes in the biological sample. The contamination detection reagent pad 120,120' may also undergo a chemical reaction when exposed to the biological sample and change color over a brief period of time. However, the contamination detection reagent pad 120,120' typically has a different type of color trajectory, different color values, different chemical reaction times, or different rates of color change than otherwise expected, indicating that the reagent paddle 100 has been exposed to a hostile environment.

The contamination detection reagent pad 120 and each CTP 110 may be treated with a chemical compound (a reagent) specifically selected to react with a specific analyte. For example, the contamination detection reagent pad 120 may be selected to react to leukocytes or glucose in a biological sample, in addition to humidity or moisture. The contamination detection reagent pad 120 may indicate contamination from a hostile environment before the diagnostic test without a biological sample and during a diagnostic test with the biological sample. The analysis of the contamination detection reagent pad 120 to detect exposure to a hostile environment can differ.

In one case, the contamination detection reagent pad 120 may change color prior to the diagnostic test without a biologic sample being applied, if it has been exposed to hostile environment, such as humidity. The color of the contamination detection reagent pad 120 may change from an expected uncontaminated color point 800 to a contaminated color point 805A shown in FIG. 8 for example. The difference between the uncontaminated color point 800 and the contaminated color point 805A can readily ascertained to detect that the contamination detection reagent pad 120 has been exposed to a hostile environment. The user can be informed of the exposure to the hostile environment before the diagnostic test begins and compromised test results are measured and shown to the user.

In other cases, the reagent paddle has been exposed to a hostile environment and it may be detected during the diagnostic testing when the contamination detection reagent pad 120 is also exposed to a biological sample. When the color measurements and results obtained from the contamination detection reagent pad 120 are outside the expected range of color values, expected rates of change, or expected amounts of change in values, or expected trajectory, etc., it indicates contamination of the contamination detection reagent pad 120 and the test paddle 100.

In one case, when the reagent paddle 100 has been exposed to a hostile environment, the contamination detection reagent pad 120 changes color according to a different color trajectory after the reagent paddle has been exposed to a biological sample. For example in FIG. 8, the color trajectory 807, representing a contamination detection reagent pad 120 exposed to a hostile environment and a biological sample, has a different slope and extends further out than that of expected color trajectories 770A, 770B, 770C, and 770D at various analyte concentrations. The expected trajectories are stored color trajectories without contamination that are associated with biological samples when the reagent paddle had not been exposed to a hostile environment. The measured trajectory of the contamination detection reagent pad 120, exposed to a hostile environment and a biological sample can be compared with the stored expected trajectories without contamination that are associated with biological samples. If significant differences are determined in the comparison, the user can be informed of the exposure to the hostile environment during the diagnostic tests before the compromised test results are shown to the user.

In yet another case, when the reagent paddle has been exposed to a hostile environment, the contamination detection reagent pad changes color to different unexpected color values after the reagent paddle has been exposed to a biological sample. For example, after chemical reactions have been completed, the color of the contamination detection reagent pad 120 is determined to be at a color point 805N. The color point 805N extends beyond final time $t_n$ at curve 750N and its final color values represented by the points from all other expected final color values at color points 772A,772B,772C,772D along the curve 750N. The different unexpected color values of the contamination detection reagent pad 120 exposed to the biological sample can be compared with stored expected color values without contamination as if the reagent paddle under test had never been exposed to a hostile environment. If significant differences are determined between color values in the comparison, the user can be informed of the exposure to the hostile environment during the diagnostic tests before the compromised test results are shown to the user.

In yet another case, when the reagent paddle has been exposed to a hostile environment, the contamination detection reagent pad changes colors at different rates or by different amounts after the reagent paddle has been exposed to a biological sample. For example in FIG. 8, the amount of change in color from color point 805B to color point 805N along the contaminated curve 807 is greater than the amount of change between the first sample 802 and the last sample 802 along the non-contaminated curve 870X. The different rates or different amounts of color change in the contamination detection reagent pad 120 can be compared with stored expected rates or stored expected amounts of color change without contamination as if the reagent paddle has never been exposed to a hostile environment.

Figure 9:
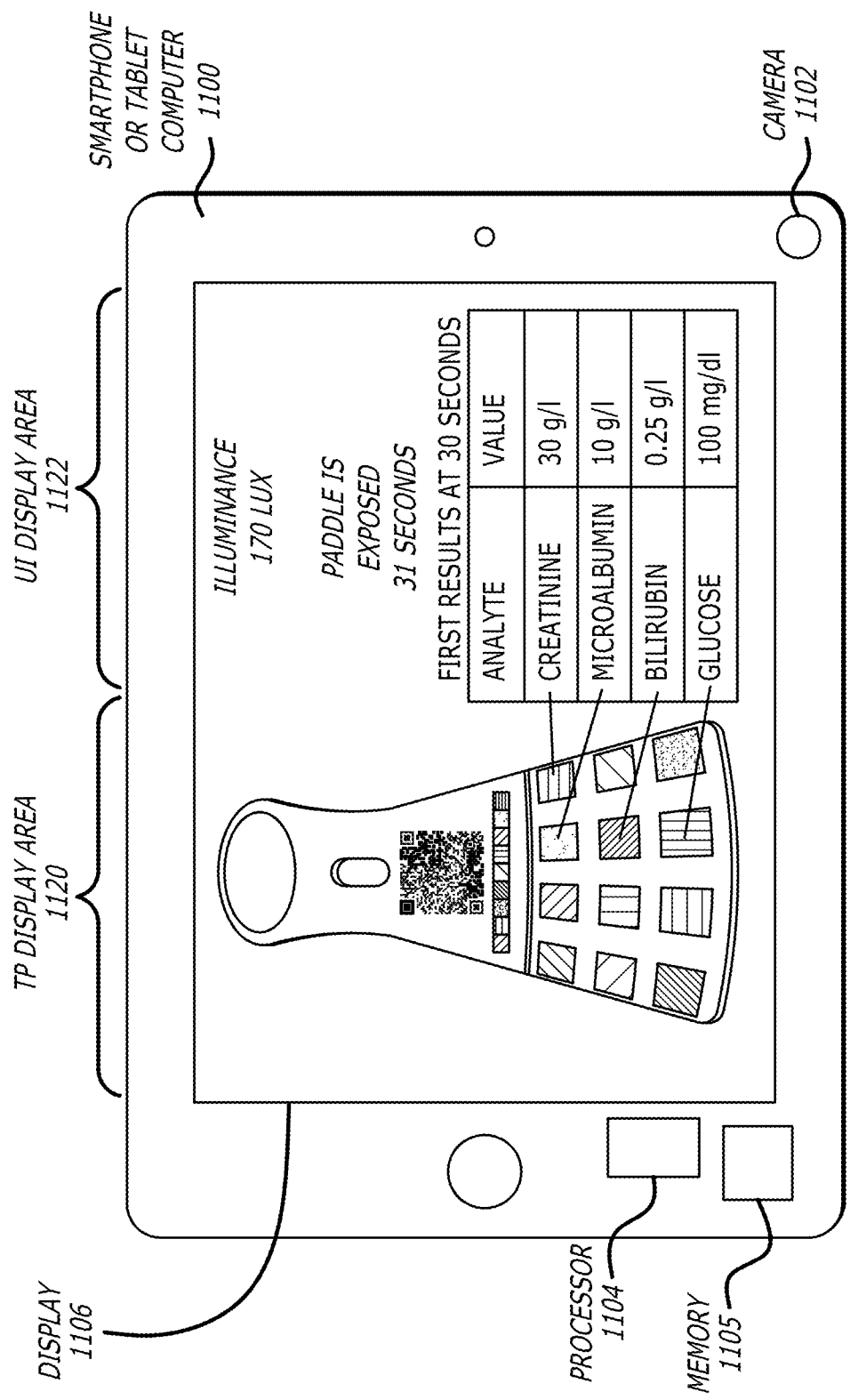
FIG. 9 is top view of a portable electronic device of a system for analyzing biological samples over time and determining a contaminated reagent paddle.

A portable electronic device with a digital camera captures color digital images of the test paddle 100. In some embodiments, an image of the paddle 100 is displayed on the portable electronic device with information and instructions for the user in a user interface. An exemplary portable electronic device 1100 is shown in FIG. 9.

Figure 2A:
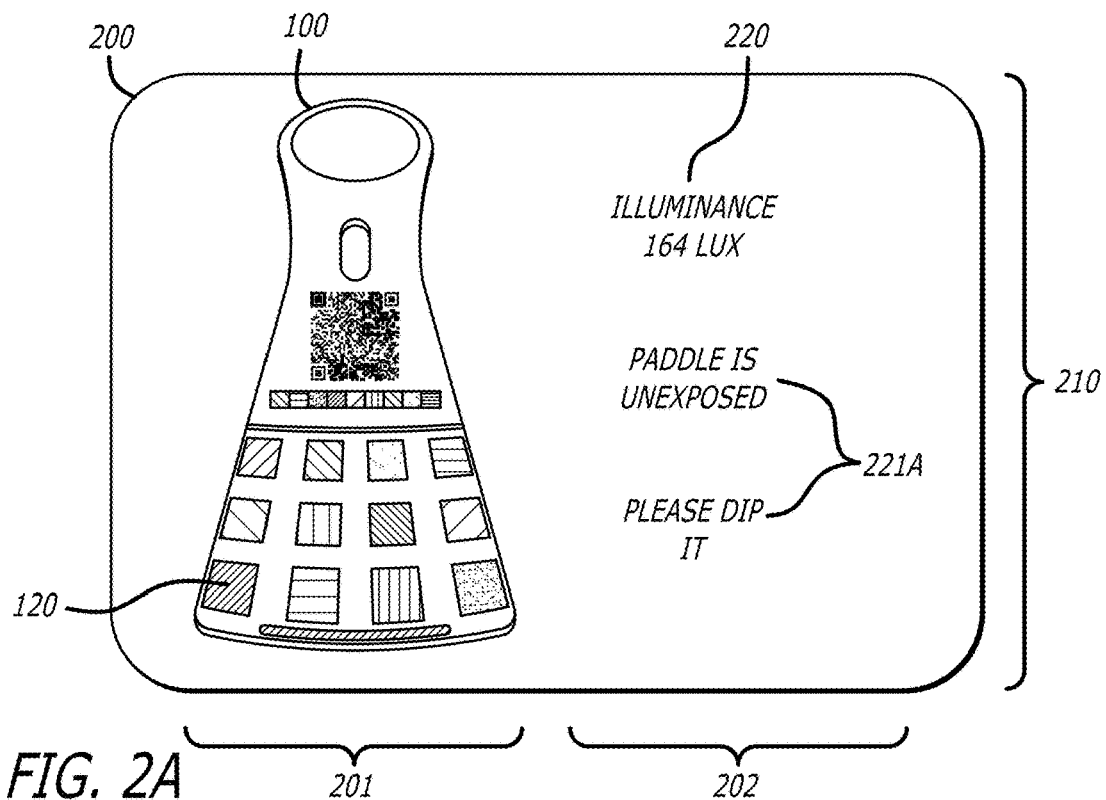
FIG. 2A is an exemplary display of a vision field showing reagent test pads of the diagnostic instrument (reagent paddle) on the left side of the display and information and instructions are shown on the right.
Figure 2B:
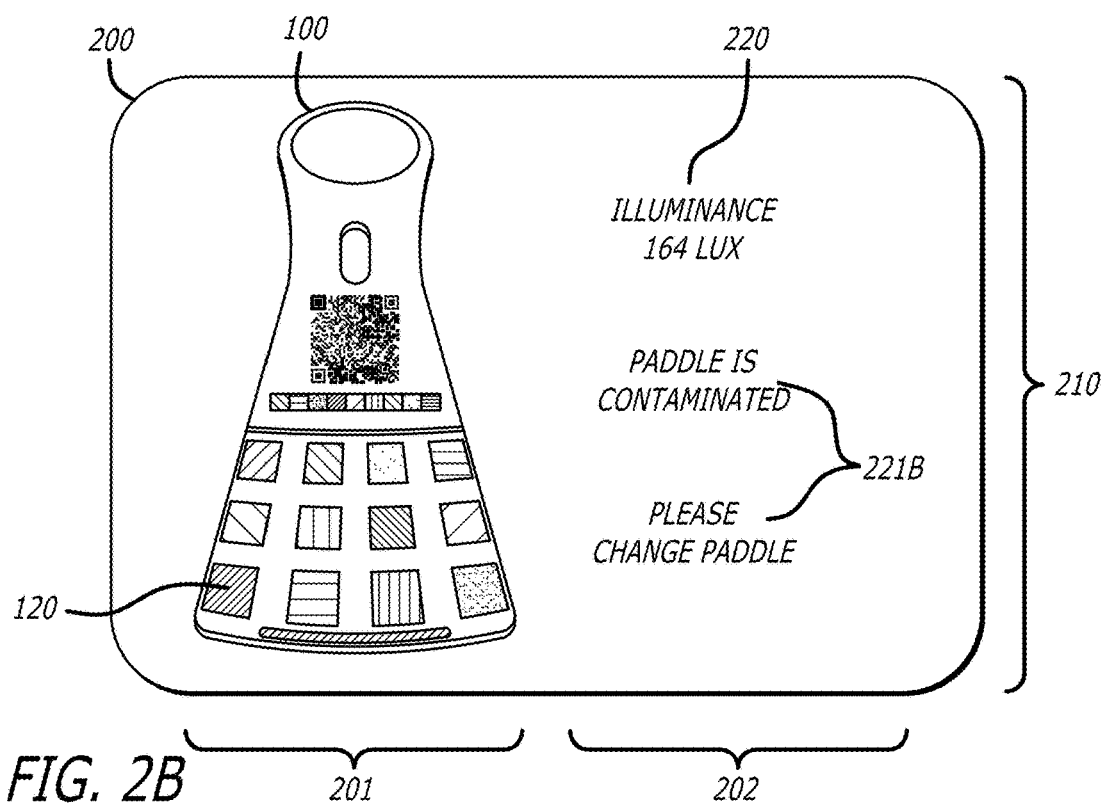
FIG. 2B is an exemplary display of a vision field showing reagent test pads of the diagnostic instrument (reagent paddle) on the left side of the display and contamination information and instructions are shown on the right.

Referring now to FIG. 2A, a field of view or vision field 200 of a display device of a portable electronic device is illustrated. The vision field 200 displays the test paddle 100 in one side 201 and a user interface (UI) 210 in an opposite side 202. FIGS. 2A-2B illustrate the reagent paddle 100 being pre-tested for contamination prior to being exposed to a biological sample that is to be tested. Generally, the user interface 210 automatically provides instructions, information, and results of the color analysis of one or more CTPs 110 as they undergo chemical reactions. However, in the pre-test phase, the user interface 210 automatically provides instructions, information, and results of the contamination detection reagent pad 120 prior to exposure to a biological sample.

The vision field 200 may be captured, displayed, and analyzed by a number of devices. However, it is desirable to make the testing and results personal and convenient by integrating the capture, display, and analysis into a user operable system so that the user can test and obtain his/her own results. The exemplary portable electronic device 1100 shown in FIG. 9 is one such system that provides for capture, display and analysis of a test paddle and its contamination and CTP pads.

In response to the color change caused by chemical reaction of the reagent in the CTPs 110 of the paddle 100, illuminance information 220 may be calculated by the methods described in Burg '397, which is incorporated herein by reference. After an analysis of the contamination detection reagent pad 120, prior to exposure by the biological sample, instructions 221A-221B shown in either FIG. 2A-2B may be displayed to the user. With no contamination detected by the contamination detection reagent pad 120, the instructions 221A (part of the user interface 210) may be displayed on the display screen to the user to guide him/her through the protocol or procedures for obtaining information from the test pads 110 of the paddle 100. The instructions 221A may indicate to the user that the test paddle 100 is unexposed to the biological sample. The instructions 221A may further instruct the user to expose the CTPs of the test paddle such as by dipping it into the biological sample and starting a timer associated with an electronic device.

Reference is now made to FIG. 2B. With contamination detected by the contamination detection reagent pad 120 prior to exposure to the biological sample, the instructions 221B can be displayed in the field of view or vision field 200 of the portable electronic device. The instructions 221B inform the user of the contamination condition of the reagent paddle 100. Due to the contamination condition, the instructions 221B further inform the user to change the paddle to a different reagent paddle 100 before exposing it to the biological sample.

To determine if the reagent paddle 100 is contaminated, an image of the reagent paddle 100 with the contamination detection reagent pad 120 is captured by the system. The location of the contamination detection reagent pad 120 is detected in the image and its color is captured. The captured color may need correction to standardize it due to differences in camera types of the current image and the stored data used for comparison. The reagent paddle 100 includes the reference color pad (RCB) 108 for the purpose color correction to that of the known standard associated with the stored data. The color of contamination detection reagent pad 120 is corrected by the captured color of one or more color samples in the reference color bar (RCB) 108 with the present camera and the stored color of the same one or more color samples in the reference color bar (RCB) captured by the known standard type of camera and standard of illumination.

The corrected color value of contamination detection reagent pad 120 can be evaluated by comparing it with a predetermined range of color values. If the corrected color value of contamination detection reagent pad 120 exceeds the predetermined range of color values, it may indicate contamination, that the contamination detection reagent pad 120 was exposed to a hostile environment. After color correction, other methods described herein may be used to determine if the contamination detection reagent pad 120 and the paddle were exposed to a hostile environment. Note however, illumination can affect the corrected color value of the contamination detection reagent pad 120. The system decides where or not contamination instructions are to be shown to the user based on the evaluation under certain illuminance conditions. The instructions 221B may indicate to the user that the reagent paddle 100 was contaminated and compromised. The instructions 221B may further instruct the user to change or use another reagent paddle.

After exposure of the paddle to a biological sample, the contamination detection reagent pad 120 may still be analyzed as described herein to determine if the contamination detection reagent pad 120 has been exposed to a hostile environment along with the paddle. FIGS. 3A-3B, 4A-4B, 5A-5B, and 6 illustrate the field of view or vision field 200 of the display device of a portable electronic device with exemplary conditions after the paddle 100 has been exposed to a biological sample.

Figure 3A:
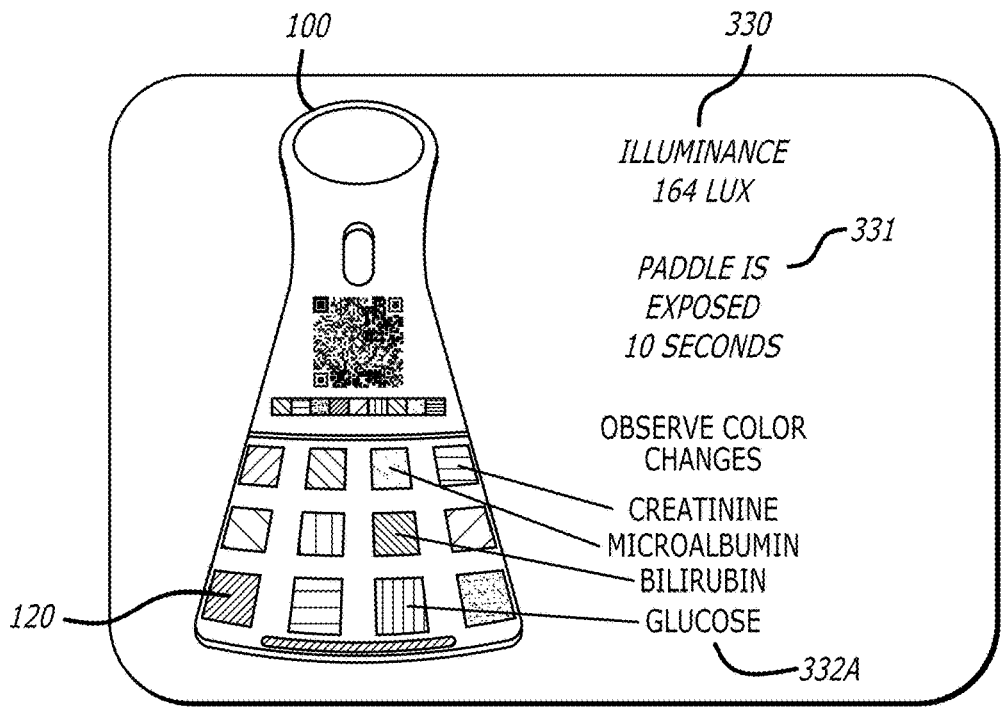
FIG. 3A is an exemplary display of a vision field showing the diagnostic instrument (reagent paddle) with its reagent test pads after a time lapse of 10 seconds.

FIG. 3A illustrates a real-time interpretation of the image data of the reagent paddle 100 after an initial lapse of time (e.g., about 10 seconds) of exposure to the biological sample. An image of the paddle 100 is displayed alongside additional information. On the left side of the vision field, the user sees the paddle 100 and the CTP chemical reaction colors evolving over time. On the right side of the vision field the user may be presented with information. For example, the information displayed may include an illuminance measurement (or luminous emittance measurement) 330 and the elapsed exposure time 331 since dipping the paddle 100 into the biological sample. In addition, instructions 332A may be provided to the user to observe the color changes in faster chemical reactions, such as for creatinine, microalbumin, bilirubin, and glucose, for example, that occurs at different CTPs 110. The real-time interpretation puts a focus on the faster chemical reactions allowing users to follow the quick reactions. In FIG. 3A, exposure to a hostile environment was undetermined by the contamination detection reagent pad 120.

Figure 3B:
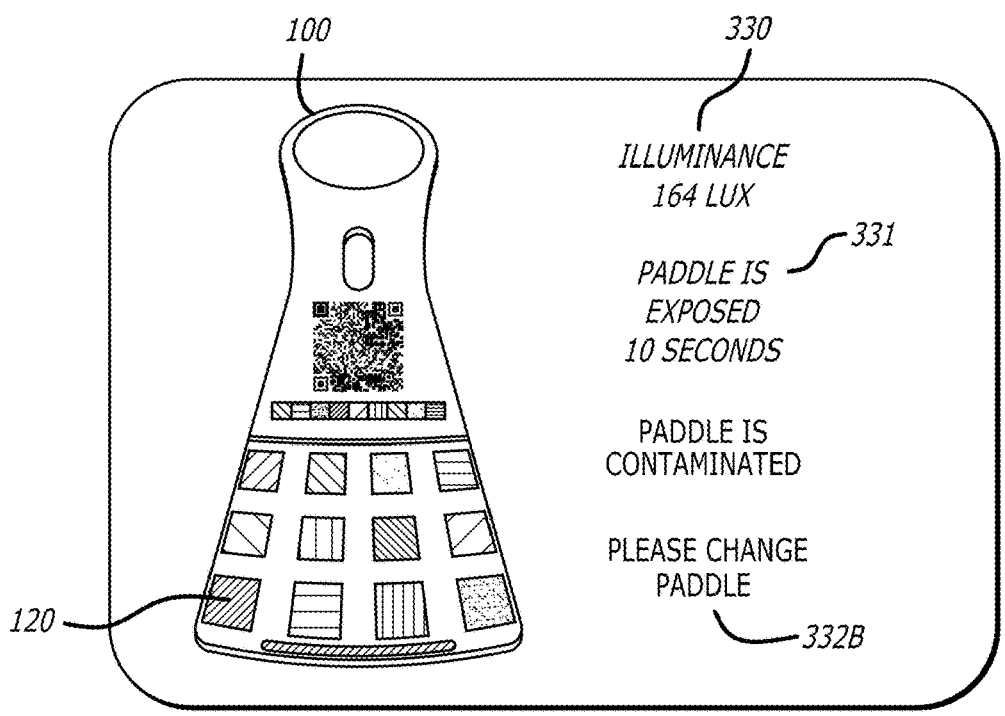
FIG. 3B is an exemplary display of a vision field showing the diagnostic instrument (reagent paddle) with its reagent test pads and contamination information and instructions after a time lapse of 10 seconds.

FIG. 3B also illustrates a real-time interpretation of the image data of the reagent paddle 100 after about 10 seconds of exposure to the biological sample. The user may forget to do a pre-exposure test. A further determination is made of the image data for the contamination detection reagent pad. The real-time examination of the reaction of the contamination detection reagent pad 120 progresses as the chemical reaction at the CTPs and their colors evolve over time. At the very beginning stage of these chemical reactions with the biological sample, color of the contamination detection reagent pad 102 can be very different if the reagent paddle under test has been exposed to any hostile environment. Accordingly, the color of the contamination detection reagent pad 102 when exposed to a hostile environment can be readily compared with the expected color of the contamination detection reagent pad 102 when unexposed to a hostile environment. Once the system detects that the color of the contamination detection reagent pad is out of a predetermined value range of color, the right side of the vision field 200 presents real-time instructions 332B to the user indicating that the reagent paddle is contaminated. No results are displayed. The instructions may further instruct the user to use another reagent paddle.

Figure 4A:
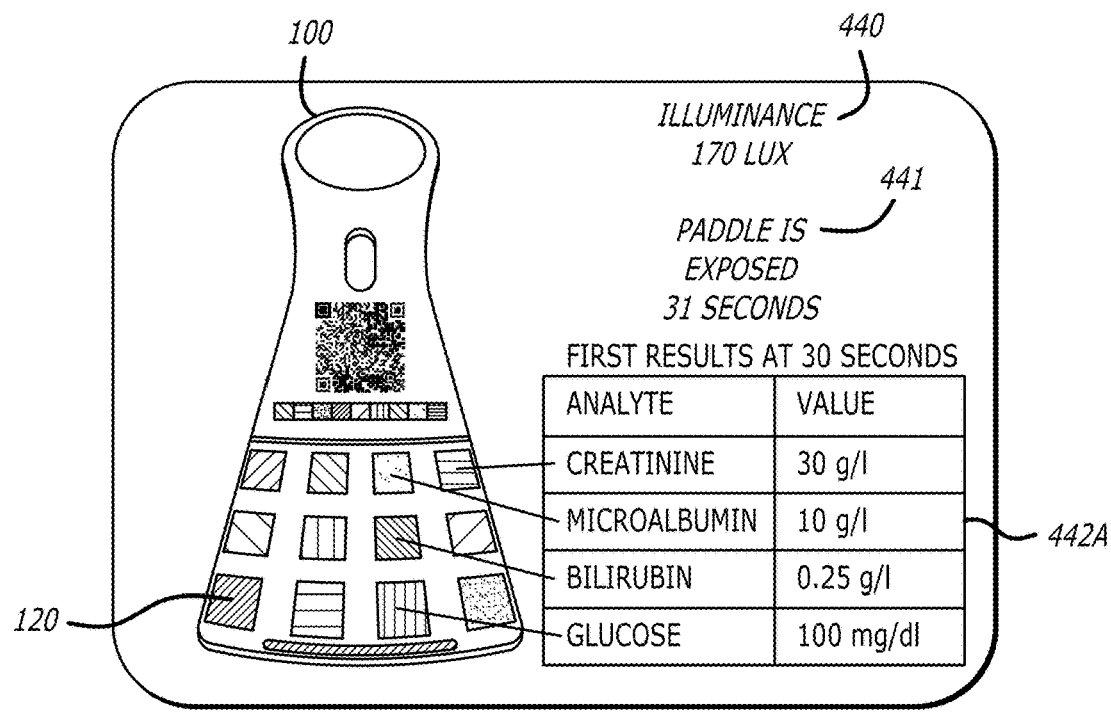
FIG. 4A is an exemplary display of a vision field showing the diagnostic instrument (reagent paddle) with its reagent test pads after a time lapse of 30 seconds.

FIG. 4A illustrates an overview of a first result interpretation after a further elapse in time, such as 31 seconds for example, of exposure to the biological sample. When the method reaches the first timeline for results interpretation, an initial table 442A of results is shown. FIG. 4A shows the paddle 100 at the left side of the visual field. The right side of the visual field adds information such as an illuminance measurement (or luminous emittance measurement) 440 and an elapsed time 441 since dipping the paddle into the biological sample. The table 442A illustrates the first results at thirty seconds for example. The values in the initial table are results for the fast reactions of the reagents of various CTPs exposed to the biological sample. Similar results may be produced for all chemical reactions and as further time elapses, therefore guiding the user in understanding the color recognition process of the CTPs. In FIG. 4A, exposure to a hostile environment was undetermined by the contamination detection reagent pad 120.

Figure 4B:
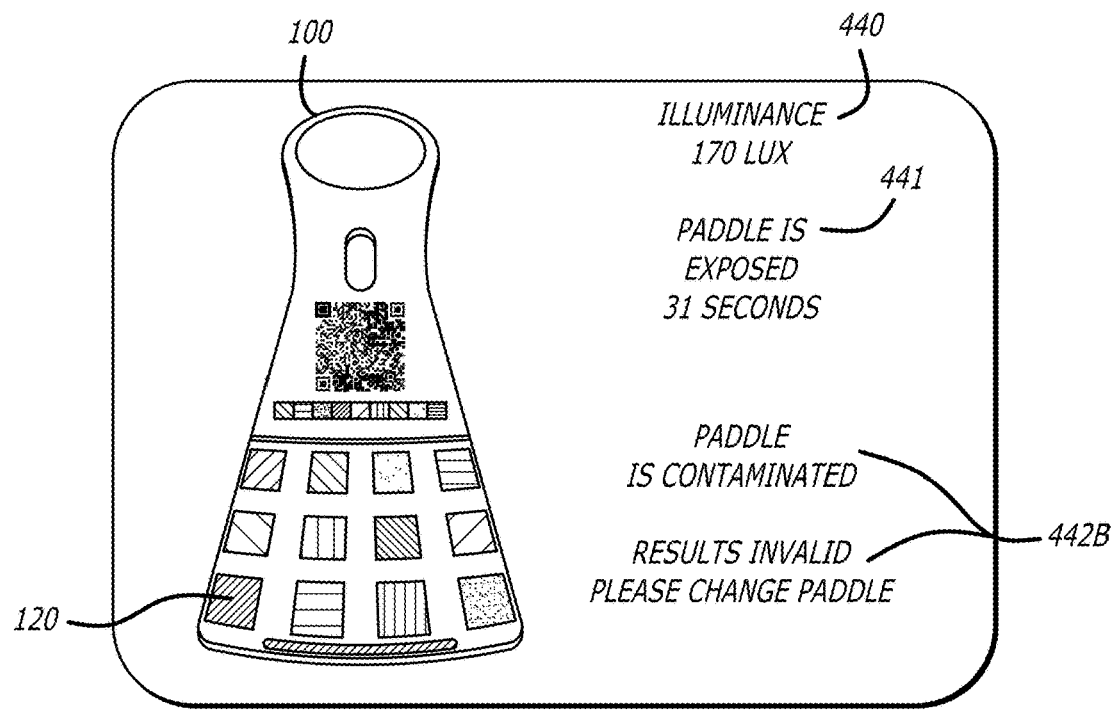
FIG. 4B is an exemplary display of a vision field showing the diagnostic instrument (reagent paddle) with its reagent test pads and contamination information and instructions after a time lapse of 30 seconds.

FIG. 4B illustrates a real-time determination of the data of the contamination detection reagent pad 120 indicating contamination after exposure to the biological sample. The real-time examination of the reaction of the contamination detection reagent pad progresses as the method reaches a first timeline for interpretation. At the first timeline for interpretation, before the initial table of results is shown to the user, a further determination is made of the image data for the contamination detection reagent pad. A determination is made and whether or not a hostile environmental condition has been experienced by the contamination detection reagent pad 120 and the paddle 100. Various methods may be used to determine the contamination of the contamination detection reagent pad over different time periods.

In one embodiment, a determination of contamination is made by comparing the corrected color of the contamination detection reagent pad with a predetermined value range of color. In another embodiment, a determination of contamination is made by comparing the difference of two corrected colors of the contamination detection reagent pad in reagent paddle images captured at different points of time. For example, one corrected color of the contamination detection reagent pad can be extracted from the image captured prior to the reagent paddle is exposed to the biological sample, and the other corrected color of the contamination detection reagent pad can be extracted from the first image captured after the reagent paddle has been exposed to the biological sample. As another example, one corrected color of the contamination detection reagent pad can be extracted from the image captured before the reagent paddle has been exposed to the biological sample, and the other corrected color of the contamination detection reagent pad can be extracted from the image captured after the reagent paddle has been exposed to the biological sample upon which the first batch of real-time results are interpreted. As yet another example, one corrected color of the contamination detection reagent pad can be extracted from the image captured from the first image captured after the reagent paddle has been exposed to the biological sample, and the other corrected color of the contamination detection reagent pad can be extracted from the image captured after the reagent paddle being exposed to the biological sample upon which the first batch of real-time results are interpreted.

After the system detects by whatever method that the color of the contamination detection reagent pad indicates contamination, the right side of the vision field presents real-time instructions 442B to the user indicating the reagent paddle is contaminated due to exposure to a hostile environment and the results are invalid. The compromised results are not shown. The instructions may further instruct the user to change to another reagent paddle to perform the test of the biological sample.

Figure 5A:
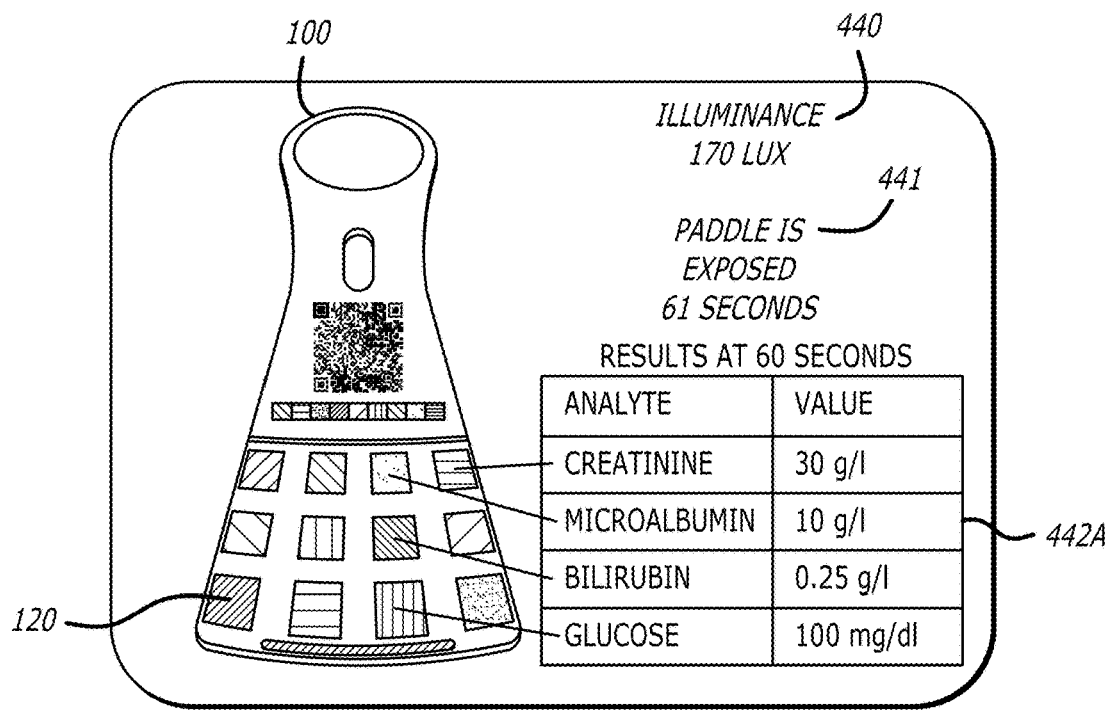
FIG. 5A is an exemplary display of a vision field showing the diagnostic instrument (reagent paddle) with its reagent test pads after a time lapse of 60 seconds.

Referring now to FIG. 5A, the test paddle 100 is shown after sufficient time has passed wherein all reactions are completed on all of the CTPs 110 after exposure to the biological sample. A table 442A, indicating results of the reagent analysis, is provided in the right field vision by the small screen display device. These results allow users to understand the reagent process as well as to easily share the results with a medical support team to obtain a diagnosis. The right side of the visual field adds information such as an illuminance measurement (or luminous emittance measurement) 440 and an elapsed time 441 since dipping the paddle into the biological sample. In FIG. 5A, exposure to a hostile environment was undetermined by the contamination detection reagent pad 120 after exposure to the biological sample so that the table 442A is displayed.

Figure 5B:
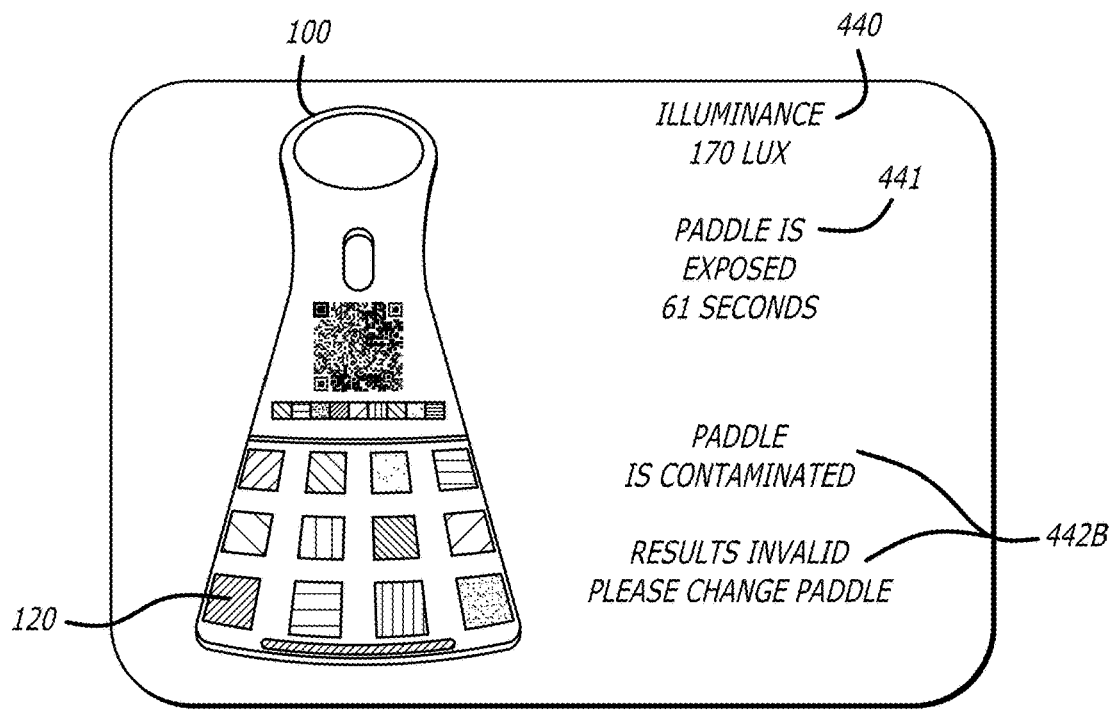
FIG. 5B is an exemplary display of a vision field showing the diagnostic instrument (reagent paddle) with its reagent test pads and contamination information and instructions after a time lapse of 60 seconds.

FIG. 5B illustrates a last real-time determination of the data of the contamination detection reagent pad 120 indicating contamination after exposure to the biological sample. The real-time examination of the reaction of the contamination detection reagent pad progresses after sufficient time has passed wherein all reactions are completed on all of the CTPs 110. Before the final table of results is shown to the user, a further determination is made of the image data of the contamination detection reagent pad. A determination is made to indicate whether or not the contamination detection reagent pad 120 and the paddle 100 were exposed to a hostile environment. Various methods of determining contamination may be made over different time periods of images of the contamination detection reagent pad.

In one embodiment, contamination is determined by comparing the corrected color of the contamination detection reagent pad at the time point of completion of chemical reactions with a predetermined value range of color. In another embodiment, a determination of contamination is made by comparing the difference of two corrected colors of the contamination detection reagent pad of reagent paddle images captured at different points of time. For example, one corrected color of the contamination detection reagent pad can be extracted from an image captured prior to the reagent paddle being exposed to the biological sample. Another corrected color of the contamination detection reagent pad can be extracted from a last image captured after the reagent paddle 100 has been exposed to the biological sample and all chemical reactions of the CTPs 110 and of the contamination detection reagent pad 120 have been completed. As another example, one corrected color of the contamination detection reagent pad can be extracted from the image captured after the reagent paddle has been exposed to the biological sample upon which the first batch of real-time result are interpreted. The other corrected color of the contamination detection reagent pad for comparison can be extracted from the last image captured after the reagent paddle has been exposed to the biological sample and all of the chemical reactions have been completed. As yet another example, one corrected color of the contamination detection reagent pad can be extracted from the image captured after the reagent paddle has been exposed to the biological sample upon which later real-time result are interpreted. The other corrected color of the contamination detection reagent pad for comparison can be extracted from the last image captured after the reagent paddle has been exposed to the biological sample and all chemical reactions have been completed.

After the system detects by whatever method that the color of the contamination detection reagent pad indicates contamination, the right side of the vision field presents real-time instructions 442B to the user indicating that the reagent paddle is contaminated by a hostile environment and the results are invalid. The compromised results are not displayed to the user in the vision field. The instructions may further instruct the user to use another reagent paddle.

Figure 6:
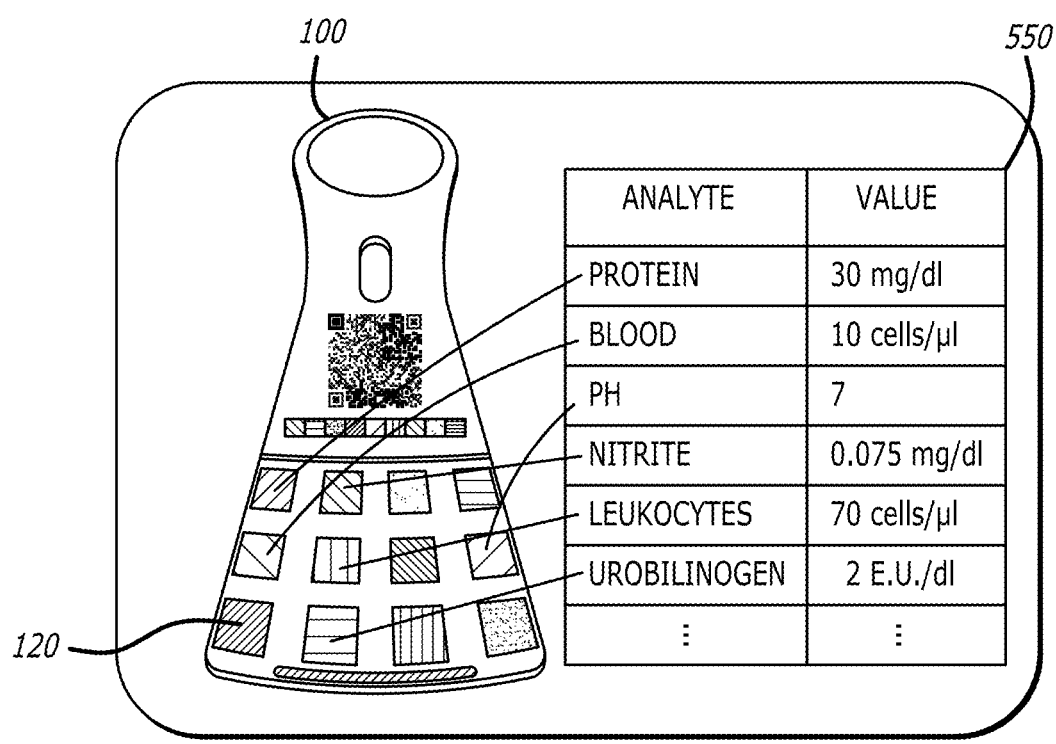
FIG. 6 is an exemplary display of a vision field showing the diagnostic instrument (reagent paddle) with its reagent test pads and a chart of analyte concentrations.

Referring now to FIG. 6, a vision field is illustrated showing the test paddle 100 with its reagent test pads 110,120. If no prior contamination has been determined after the test paddle 100 has been exposed to the biological material/fluid being tested, and the chemical reactions of the contamination detection medium are completed and the test reagent media are completed with the biological material/fluid being tested, a chart of analyte concentrations is also finally displayed beside the test paddle 100. The vision field including the test paddle and chart of analyte concentrations is displayed by a display device of an electronic device.

Figure 7A:
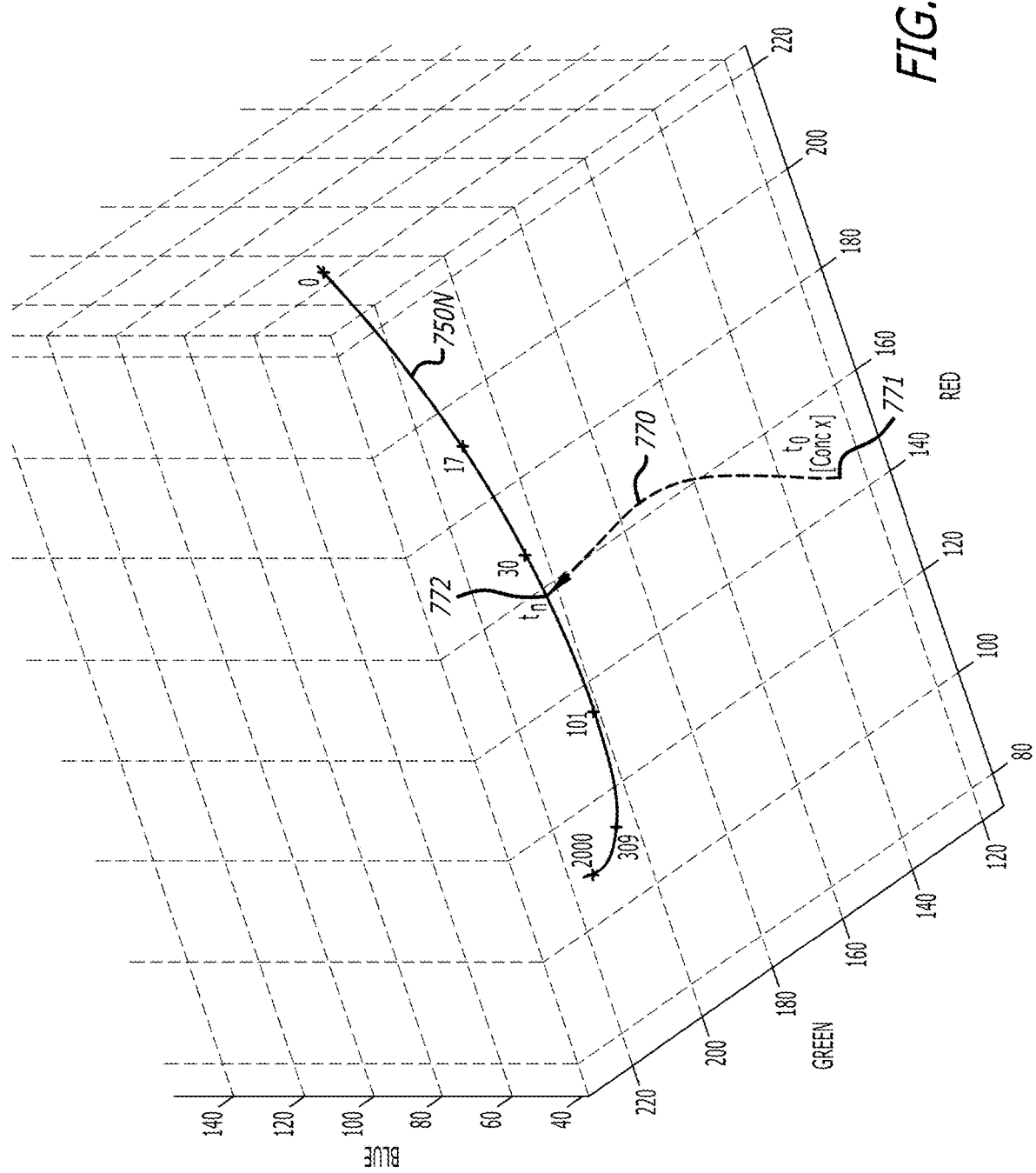
FIG. 7A is a three dimensional red, green, blue (RGB) color space graph showing a color trajectory of a chemical reaction between contamination detection reagent and an analyte.

FIG. 7A illustrates an ideal chemical trajectory 770 for an analyte reaction with the contamination detection reagent of the pad 120 over time (from time $t_0$ to $t_n$) when the reagent paddle 100 has not been exposed to any hostile environment. A method of assessing the chemical reaction taking kinetics and time into account was disclosed in U.S. patent application Ser. No. 14/419,939 and is incorporated here by reference.

The contamination detection reagent pad 120, together with the reagent paddle 100 under test, is dipped for a few seconds into a biological sample with analyte of concentration X (Cone X) at time $t_0$. The color of the contamination detection reagent pad is measured at time $t_0$ and reported into the RGB space at measured point 771. The chemical reaction between the reagent of the pad 120 and the analyte in the biological sample continues towards an asymptotic value, according to its kinetics. Eventually colors stabilize at a final measurement of time, time $t_n$, marking the end of the chemical reaction between the reagent of the contamination detection reagent pad and the analyte in the biological sample. The final measurement is plotted in the graph shown in FIG. 7A by measured point 772.

The measured point 772 is the intersection between the kinetic reaction of the reagent at a final measurement of time and a color calibration curve 750N. The color calibration curve 750N may be provided by the manufacturer of the test pad for a given analyte in the test paddle. The color calibration curve 750N represents the color of the contamination detection reagent pad 120 associated with various concentration levels of the analyte at a given time $t_n$. Accordingly, the color calibration curve 750N may also be referred to herein as a color-mass calibration curve. The trajectory 770 between the measured points 771-772 represents the change or evolution of color of the test pad over time, from time $t_0$ to time $t_n$, for a concentration X of a given analyte in a biological sample. Accordingly, the trajectory 770 may also be referred to herein to as a color evolution trajectory.

Referring now to FIG. 7B, a three dimensional color time evolution graph for a given analyte of the contamination detection reagent pad 120 is shown. In this case, the contamination detection reagent pad 120 has not been exposed to any hostile environment. The three dimensional color time evolution graph includes a plurality of color calibration curves 750A-750N in RGB color space for a given analyte over a range of time $t_0$ through tn. The three dimensional color time evolution graph further includes a plurality of color evolution trajectories 770A-770D per concentration in RGB color space for a given analyte. The graph of the color evolution trajectory curves 770A-770D illustrate how different reaction rates for different concentrations (e.g., concentration 1 (Cone 1) to concentration 4 (Cone 4)) of analyte are associated with the color change in RGB color space of the contamination detection reagent pad over time.

Given a contamination detection reagent test pad 120, various concentrations (e.g., concentration 1 (Cone 1) to concentration 4 (Cone 4)) for an analyte reflect a unique initial color point 760A-760D in the RGB space at time $t_0$ immediately after the biological sample is applied. The initial unique colors for the various concentrations form the initial color calibration curve 750A. The initial unique colors of the contamination detection reagent test pad evolve over time to further form the color calibration curve 750B at time t1 through the color calibration curve 750N at time tn. At time tn, the contamination detection reagent pad has reached is final color at a point 772A-772D along the color calibration curve 750N for the various concentrations of analyte. Along color calibration curve 750N, the reaction has reached its asymptote and the color of contamination detection reagent pad has reached its final color level at the point 772A-772D during the testing period of the paddle.

The color evolution trajectory in time for a given concentration (e.g., Conc 1, Conc 2, Conc 3, Conc 4) is represented by the curves or trajectories 770A-770D shown by dotted lines in FIG. 7B. Therefore, color evolution trajectories 770A-770D are used by the embodiments to make accurate predictions of color-time evolution. Color-time evolution has a one-to-one correspondence to the evolution of the reaction rate k of a mass or concentration of an analyte over time.

FIG. 7B represents color calibration curves 750A-750N for a contamination detection reagent pad and corresponding analyte. A similar three dimensional graph with multiple color calibration curves and color evolution trajectories can be formed for other reagents which could be used to detect exposure to hostile environments and their respective analyte, as well as analytes in a biological sample. In the reagent paddle 100, for example, one pad location may be used as the contamination detection reagent pad 120 and the manufacturer provides the sets of graph of color calibration curves for the contamination detection reagent and corresponding analyte.

A plurality of known concentrations can be used to generate a plurality of known color-time evolution trajectories corresponding to known concentrations or masses in a biological sample measured by the analyte pad. FIG. 7B, for example, illustrates a plurality of color-time evolution trajectories 770A-770D of an analyte pad for known or given mass or concentrations 760 of an analyte in a biological sample, including concentration 1 (Cone 1), concentration 2 (Cone 2), concentration 3 (Cone 3), and concentration 4 (Cone 4).

Figure 8:
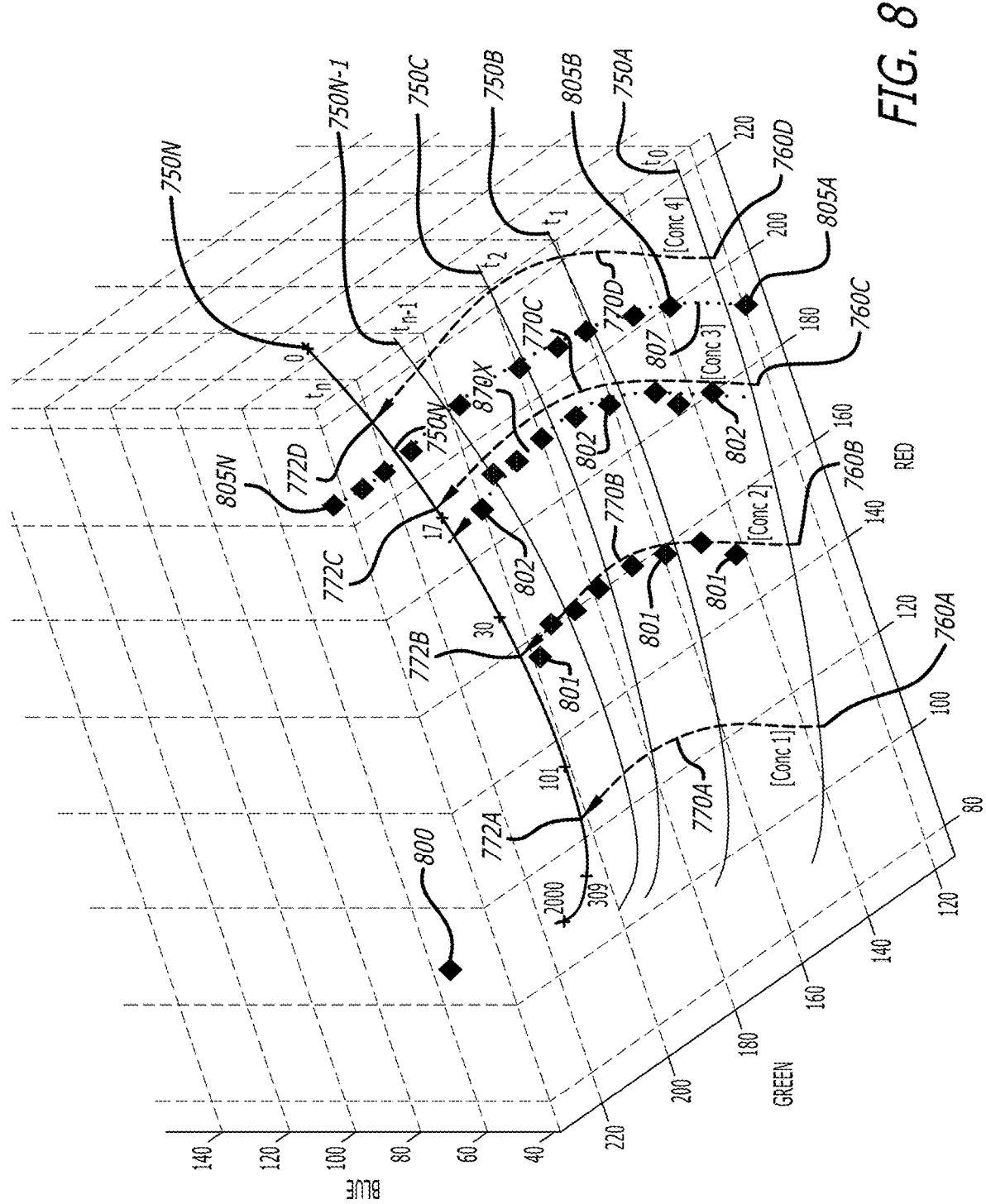
FIG. 8 is a three dimensional RGB color space graph of analyte calibration curves at multiple concentrations with measured reaction points of a contamination detection reagent pad.

Referring now to FIG. 8, a three dimensional (3D) chart of colors is shown to further explain how to detect and determine whether or not a contamination detection reagent pad has been exposed to a hostile environment and the reagent paddle has compromised. The system generates values for a curve in real time representing the color-time evolution for a concentration of analyte that detects contamination, based on the sequence of digital pictures or photos (digital images) captured at times $t_0$ through $t_n$. Each digital image represents one of a plurality of measurement points in the color space (e.g., RGB color space) along a color-time evolution curve.

At any point in time prior to the reagent paddle being exposed to a biological sample and or at the beginning stage of the reaction between the contamination detection reagent and an analyte of the biological sample, if the measurement points fall out of a standard zone of the color under certain concentration (Cone X) at the specific point of time, e.g. $t_0$ through tn, it can be determined that the contamination detection reagent pad has been exposed to a hostile environment and the reagent paddle has compromised.

If no contamination is initially found, the system continues to capture, process, and calculate differences between colors at two different critical points of time to determine if the contamination detection reagent pad has been exposed to a hostile environment and by extension the entire reagent paddle has been compromised such that results would be invalid. Two different critical points may be for example, time $t_0$ and the time at the beginning stage of the reaction between the contamination detection reagent and an analyte of the biological sample. Alternatively, two different critical points may be for example, the time at the beginning stage of the reaction between the contamination detection reagent and an analyte of the biological sample and the time at the final point of the reaction between the contamination detection reagent and the analyte of the biological sample.

If the calculated color value for the contamination detection reagent pad falls outside of a standard zone of the color difference under a certain concentration (Cone X), it may be determined that the contamination detection reagent pad has been exposed to hostile environment and the reagent paddle has been compromised. For example, a first user with a first concentration of analyte is measured and produces a first sequence of digital images over time with a changing color represented by measured points 801 adjacent curve 770B. With the measured points 801 being within the standard zone of color, the system may reach the conclusion that the reagent paddle has not been compromised. As another example, a second user with a second concentration of analyte is measured and produces a second sequence of digital images of the contamination detection reagent pad on the paddle over time with a changing color represented by measured points 805A-805N over time from pre-$t_0$ through tn and beyond to post tn. Because the color values of the measured color points 805A-805N exceed the expected standard zone of color, the system may reach the conclusion that the reagent paddle has been contaminated by hostile environment and the paddle and CTPs have been compromised.

In practice by means of a graphical manner, with a color calibration graph including a plurality of color calibration curves, the concentration of the reacting analyte in the sample is directly accessible by the intersection between a color-time evolution trajectory (aka, a time-resolved trajectory 870X) and the color calibration curves 750A-750N over time. Upon the decision of the concentration of the reacting analyte, the system knows to which kinetic curve shall it compare to and determine if the measurement points fall out of its standard zone or not.

Referring now to FIG. 9, a portable electronic device 1100 with a camera 1102 may be used to obtain test results from a diagnostic paddle 100 exposed to a biological sample or otherwise contaminated. The portable electronic device 1100 may be a smartphone or a tablet computer that has the camera 1102. For example, the portable electronic device 1100 could be any kind of smartphone (e.g., APPLE IPHONE, BLACKBERRY), handheld computer (e.g., APPLE IPAD), or any type of personal computer, network computer, workstation, minicomputer, mainframe or the like running any operating system, such as any version of ANDROID, LINUX, WINDOWS, WINDOWS NT, WINDOWS 2000, WINDOWS XP, MACOS, UNIX, SOLARIS, ARM OR IOS operating systems.

The portable electronic device 1100 may further include a display device 1106 that is used to display the test results from the diagnostic paddle 100. The display device 1106 may provide a split screen with a test paddle display area 1120 to display the test paddle 100 and a user interface display area 1122 to display instructions and results to the user.

The portable electronic device 1100 further includes a processor 1104 and a memory 1105 to store instructions for execution by the processor. The instructions may be software that provide the user interface in the UI display area 1122 and performs the algorithms and the methods described herein to obtain results.

A system may include the portable electronic device 1100 and its functional components and various processing steps. It is noted that the functional blocks may be realized by any number of hardware and/or software components configured to perform specified functions. In a preferred and non-limiting embodiment, the functional components and processing steps are associated with and/or performed using the portable electronic device 1100. For example, the embodiments may employ various integrated circuit components (e.g., memory elements, processing elements, logic elements, lookup tables, and the like), which may carry out a variety of functions under the control of one or more processors or other control devices. Similarly, the software components of the embodiments may be implemented with any programming or scripting languages such as C, C #, C++, JAVA, assembler, extensible markup language (XML), or extensible style sheet transformations (XSLT). The various algorithms may be implemented with any combination of data structures, objects, processes, routines, or other programming elements. In one non-limiting embodiment, it is envisioned that the functional components and processing steps will be included with and/or performed using the portable electronic device 1110.

In that case, the portable electronic device 1100 includes the processor 1104 that is configured to execute program instructions stored on computer-readable media 1105 associated with the portable electronic device 1100. The computer-readable media 1105 may include computer storage media, such as media implemented in any method or technology for storage of information, such as computer-readable instructions, data structures, program modules, or other data, random access memory (RAM), read only memory (ROM), electrically erasable programmable read only memory (EEPROM), flash memory, or other memory technology, CD-ROM, digital versatile disks (DVDs), or other optical disk storage, magnetic cassettes, magnetic tape, magnetic disk storage, or other magnetic storage devices, or any other medium which can be used to store the desired information and which can be accessed by an electronic device, such as portable electronic device 1100.

In certain non-limiting embodiments, the processor 1104 includes a digital image analyzer for identifying regions of a digital image containing relevant data, color correcting the digital image, and comparing the corrected portions of the digital image to table entries of the MICC to determine test results. The processor 1104 may further control a reference tag reader configured to identify and extract information from an identifier 105 affixed to or associated with the diagnostic instrument 100. The processor 1104 may further control the display 1106 connected to or associated with the portable electronic device 1100 for presenting information such as instructions for using the diagnostic instrument and test results to a user. The processor 1104 may further include and control a timer for measuring the time between when the diagnostic instrument 100 is exposed to a biological fluid sample and when the digital image of the diagnostic instrument 100 is captured. Additionally, in certain embodiments, the processor 1104 controls a data entry device (e.g., a touch screen of the display device 1106) allowing a user to enter additional information, including patient history information, symptoms, and physical characteristics of the user. The data entry device may include any input device or user interface as is known in the art, which allows a user to control an electronic device including, but not limited to, gestures on a touch-screen or any other actions that cause a change in readings obtained from sensors, keypad presses, and the like.

In addition to storing the program for controlling functions of the portable electronic device 1100, the computer-readable media 1105 may also store data including a plurality of Manufacturing Interpretation Color Chart (MICC) tables for use in urinalysis with colors that can be captured by the diagnostic instrument to determine test results. The computer readable media 1105 may also store raw or preprocessed images obtained by the camera sensor 1102, decision trees for determining a patient condition, and other input data necessary for executing functions of the programs used to analyze the diagnostic instrument 100 and its CTPs 110, and at least one contamination detection pad 120.

When implemented in software, the elements of the embodiments of the invention are essentially the code segments or instructions executed by a processor (e.g., processor 1104 in FIG. 9) to perform the necessary tasks. The program or code segments can be stored in a processor readable medium. The "processor readable medium" may include any medium that can store information (e.g., memory 1105 in FIG. 9). Examples of the processor readable medium include an electronic circuit, a semiconductor memory device, a read only memory (ROM), a flash memory, an erasable programmable read only memory (EPROM), a floppy diskette, a CD-ROM, an optical disk, a hard disk, a fiber optic medium, a radio frequency (RF) link, etc. The program or code segments may be downloaded from another storage device using a computer data signal embodied in a carrier wave over a transmission medium or a communication link. The computer data signal may include any signal that can propagate over a transmission medium such as electronic network channels, optical fibers, air, electromagnetic, RF links, etc. The code segments may be downloaded using such computer data signals via computer networks such as the Internet, Intranet, etc.

While certain exemplary embodiments have been described and shown in the accompanying drawings, it is to be understood that such embodiments are merely illustrative of and not restrictive on the broad invention, and that the embodiments of the invention not be limited to the specific constructions and arrangements shown and described, since various other modifications may occur to those ordinarily skilled in the art. For example, the embodiments shown and described herein describe a contamination pad and analytes of reagent test pads for urinalysis of urine. The embodiments of the invention can function and be performed with a contamination pad and analytes of reagent test pads for the analysis of blood. Furthermore, embodiments have been described with respect to an RGB color space. Those of ordinary skill in the art will recognize that embodiments of the invention may be practiced with other types of color spaces such as Cyan-Magenta-Yellow-Key (CMYK), pantone, Munsell, International Commission on Illumination (CIE) XYZ, or the International Color Consortium (ICC) device independent color space (L*a*b color space). Accordingly, the embodiments of the invention should not be construed as being limited by such illustrated embodiments, but rather construed according to the claims that follow below.

What is claimed is:

1. A reagent paddle comprising:
   a color reference including a plurality of reference samples of different colors;
   a plurality of test mediums, each test medium of the plurality of test mediums including a different reagent associated with a different analyte, the different reagent of each test medium being configured to change color, when exposed to a fluid sample, in response to presence of a respective analyte in the fluid sample; and
   at least one contamination detection medium including a reagent, the reagent in the at least one contamination detection medium being configured to change color, before the plurality of test mediums are exposed to the fluid sample, in response to being exposed to a contamination resulting from contact with a human body, wherein the contamination is different from the fluid sample being tested.

2. The reagent paddle of claim 1, further comprising:
   a handle;
   a neck region coupled to the handle, the neck region including the color reference; and
   a test region coupled to the neck region, the test region including the plurality of test mediums and the at least one contamination detection medium.

3. The reagent paddle of claim 2, wherein
   the neck region further includes an identifier including identifying information about the paddle.

4. The reagent paddle of claim 3, wherein
   the neck region further includes a slot.

5. The reagent paddle of claim 2, wherein
   the plurality of test mediums include multiple chemical test pads arranged in a plurality of rows and columns.

6. The reagent paddle of claim 3, wherein
the at least one contamination detection medium is at least one contamination test pad located amongst the plurality of rows and columns of chemical test pads.

7. The reagent paddle of claim 5, wherein
the at least one contamination detection medium is a contamination test bar spaced apart from the plurality of rows and columns of chemical test pads.

8. The reagent paddle of claim 1, wherein
the plurality of test mediums are chemical test pads arranged into a plurality of rows and columns.

9. The reagent paddle of claim 8, wherein
the at least one contamination detection medium is at least one contamination test pad located amongst the plurality of rows and columns of chemical test pads.

10. The reagent paddle of claim 8, wherein
the at least one contamination detection medium is a contamination test bar spaced apart from the plurality of rows and columns of chemical test pads.

\* \* \* \* \*